United States Patent
Wadhwa (12)

(10) Patent No.: US 6,642,276 B2
(45) Date of Patent: Nov. 4, 2003

(54) CONTROLLED RELEASE MACROLIDE PHARMACEUTICAL FORMULATIONS

(75) Inventor: Hardeep Wadhwa, Panchkula Haryana (IN)

(73) Assignee: M/S Ind-Swift Limited (IN)

( * ) Notice: Subject to any disclaimer, the term of this patent is extended or adjusted under 35 U.S.C. 154(b) by 0 days.

(21) Appl. No.: 10/261,564

(22) Filed: Sep. 30, 2002

(65) Prior Publication Data

US 2003/0077325 A1 Apr. 24, 2003

(30) Foreign Application Priority Data

Oct. 1, 2001 (IN) ..................... 1019/Del/2001
Oct. 1, 2001 (IN) ..................... 1018/Del/2001

(51) Int. Cl.$^7$ ............ A61K 47/00; A61K 9/48; A61K 9/20; A61K 9/14; A61K 9/36

(52) U.S. Cl. .............. 514/781; 514/772.4; 514/778; 514/777; 424/400; 424/451; 424/452; 424/457; 424/463; 424/464; 424/465; 424/468; 424/474; 424/476; 424/479; 424/482; 424/489; 424/480; 424/490

(58) Field of Search ............... 424/400, 451, 424/452, 457, 463, 464, 465, 468, 474, 489, 490, 480, 476, 479, 482; 514/772.4, 777, 778, 781

(56) References Cited

U.S. PATENT DOCUMENTS

| 4,842,866 A | * | 6/1989 | Horder et al. |
| 5,457,111 A | * | 10/1995 | Luly et al. |
| 5,705,190 A | * | 1/1998 | Broad et al. |
| 5,750,510 A | * | 5/1998 | Elliott et al. |

FOREIGN PATENT DOCUMENTS

| JP | 10335732 | * | 11/1998 |
| WO | 00/02567 | * | 1/2000 |
| WO | 00/48607 | * | 8/2000 |
| WO | 01/26663 | * | 4/2001 |
| WO | 01/49246 | * | 7/2001 |

* cited by examiner

Primary Examiner—Thurman K. Page
Assistant Examiner—Humera N. Sheikh
(74) Attorney, Agent, or Firm—Knobbe, Martens, Olson & Bear LLP

(57) ABSTRACT

Disclosed is an oral controlled release macrolide pharmaceutical formulation. In a preferred embodiment, the formulation comprises a citrate salt of a preferred macrolide, clarithromycin. Also disclosed are methods for preparing, isolating and characterizing soluble and stable citrate salt of macrolides and use thereof in all solid dosage forms of macrolides.

41 Claims, 5 Drawing Sheets

Comparative Dissolution profiles of Clarithromycin in its Controlled release tablet-500mg made by different methods

Comparative Dissolution profiles of Clarithromycin in its Controlled release tablet-500mg in different batches made by using Clarithromycin Citrate Salt Comparative Dissolution Profile of Clarithromycin in its Controlled release tablet (500mg) using the Physical Mixture, stored at Room Temperature (RT) and at 40°C/75% RH for 4 months

CONTROLLED RELEASE MACROLIDE PHARMACEUTICAL FORMULATIONS

RELATED APPLICATION INFORMATION

This application claims priority under 35 U.S.C. §119 (a)–(d) to Indian Provisional Patent Application Nos. 1018/DEL/2001 and 1019/DEL/2001, filed Oct. 1, 2001.

BACKGROUND OF THE INVENTION

1. Field of the Invention

This invention in general relates to soluble and stable citrate salts of macrolides and processes for preparing, isolating and characterizing such salts and use thereof in all solid dosage forms of macrolides. In a preferred embodiment, the salts are used in oral controlled slow release solid pharmaceutical formulations, such as a once daily formulation of clarithromycin.

2. Description of the Related Art

The advantages of Controlled Release Dosage Forms for extended or sustained action are well known i.e. reduced daily dosage, patient convenience and improved patient compliance, especially in the case of very bitter-tasting drugs e.g. erythromycin and its derivatives. These macrolide antibiotics are known for their anti-bacterial activity against a number of micro-organisms and are typically administered as Immediate Release (IR) compositions, two or three times a day, for a regimen of 10 to 14 days. Clarithromycin, (6-O-methylerythromycinA) in particular, has a very bitter metallic taste which can result in poor compliance of the regimen or selection of another, possibly a less effective therapeutic agent.

An approach to address the possible non-compliance with the regimen is to develop controlled release solid preparations containing erythromycin derivatives. Unfortunately the properties of these macrolides, like many other poorly soluble basic drugs did not allow them to be incorporated in a single oral dosage form to provide a controlled efficient release of drug throughout a 24 hrs. period with reproducible bioavailability. The reason being that these erythromycin derivatives are slightly alkaline, practically water insoluble and acid-sensitive drugs. A basic drug's solubility decreases with increasing pH as it proceeds distally towards the large intestine (pH 6 to 8), while it is soluble in stomach (pH 1.2) and upper or proximal region of small intestine (pH 5). Thus a poorly soluble basic drug will lead to less drug being available for absorption in lower or distal intestine. A daily dose of 500 mg of clarithromycin has to be incorporated in a relatively small matrix for the convenience of swallowing, thus leaving a relatively small space for the optimization of biopharmaceutical and physicochemical properties of a formulation. Consequently in the preparation of a 24 hrs. tablet, there arises the problem of high dose of poorly soluble clarithromycin along with the need to ensure its reproducible and pH independent release continuously from the dosage form as it proceeds through the GI tract.

U.S. Pat. No. 4,842,866 discloses the development of a controlled release formulation of erythromycin derivatives using an alginate matrix comprising a water soluble alginate and a complex salt of alginic acid, having one cation that yields a soluble alginate salt and another cation that alone yields an insoluble alginate salt. However, in vivo animal studies showed that reproducibly bioavailable controlled release formulations of macrolide antibiotics were not possible using alginates or any other monolithic hydrogel tablet due to their inherent problems of acid instability, poor drug solubility and variable and pH dependent GI transit. A major approach, which has been used since then to improve the bioavailability of erythromycin derivatives, is the use of an organic acid e.g. citric acid along with the poorly soluble basic drug in the form of physical mixture in a solid dosage form. This approach has been disclosed in Japanese Patent No. 163823 and this has been referred in the U.S. Pat. No. 5,705,190 and it has been believed that the formulation with the organic acid creates a micro-environment of low pH to enhance the solubility of the drug within the dosage form as it moves down the GI tract. Although the use of citric acid solved the problem of poor and variable GI absorption of macrolides, the problem of acid-instability still remained in these formulations as clarithromycin and free citric acid are in the vicinity of each other in these dosage forms. On one hand, clarithromycin, roxithromycin and other erythromycin derivatives are reported to be acid-sensitive drugs, while on the other hand, they are being used in direct contact with acids in these oral solid formulations.

An oral formulation containing a physical mixture of 6-0-methyl erythromycin A and citric acid with improved bioavailability has been disclosed in Japanese Patent No. 163823/1985.

U.S. Pat. No. 5,705,190 describes a solid oral pharmaceutical formulation with controlled release containing a drug poorly soluble in water, a water soluble alginate salt, a complex salt of alginic acid with a metal cation and an organic carboxylic acid facilitating the dissolution of the drug.

Japanese Patent No. 89/42,625 describes the preparation of film coated microgranules of a drug with sustained action, which in addition to clarithromycin also contain AEA and water.

International Publication No. WO 01/26663A1 describes a pharmaceutical formulation with extended action containing an erythromycin derivative and a hydrophilic water soluble polymer, showing at oral administration, an improved taste profile and fewer gastrointestinal side effects in comparison to the usual formulation.

International Publication No. WO 00/48607 describes an improved pharmaceutical formulation for controlled release of clarithromycin or its derivative, enabled by a novel combined matrix consisting of a fatty and a hydrophilic component, where to also a surfactant and a pH modulator may be added when an additional influence on the release profile of the active substance is desired.

International Publication No. WO 00/02567 describes water miscible pharmaceutical compositions containing up to about 40% of a macrolide such as an azalide antibiotic prepared by reaction of macrolide with acid in a non-aqueous water miscible organic solvent system.

International Publication No. WO 01/49246A2 covers the sustained release tablets containing Hydroxy Propyl Methyl Cellulose as Matrix material and clarithromycin as active ingredient.

Therefore there exists the need for developing a pharmaceutical composition of poorly soluble basic drugs, especially of macrolide antibiotics, which overcomes all their problems of poor solubility, pH-dependent solubility and irreproducible bioavailability, without having the problem of instability of drug due to the use of its physical mixture with citric acid. Also there exists a need to address two additional problems in controlled release dosage forms of macrolides i.e. (a) Slowing down of release of drug with aging from the mixture of citric acid and alginate matrix and (b) Non- Repeatable Dissolution Profiles of different batches of the above mentioned dosage form, as disclosed in Patent No. WO/00/48607.

SUMMARY OF THE INVENTION

The present application provides for a soluble and stable form of macrolide and its dosage forms thereof. In preferred embodiments, there are provided isolated citrate salts of macrolides in their oral controlled slow release solid formulations useful for reducing the daily dosage regimen and especially to a once daily formulation of clarithromycin.

In one embodiment, there is provided a controlled release pharmaceutical formulation comprising a macrolide citrate salt, at least one hydrophilic polymer, a binder, a filler and a lubricant, wherein the macrolide citrate salt is obtained by dispersing a macrolide in an organic solvent, adding an aqueous solution comprising an equimolar amount of citric acid to the macrolide, and evaporating the organic solvent.

In another embodiment, there is provided a method for producing a controlled release pharmaceutical formulation of macrolide citrate salt. The method comprises mixing multiple components comprising a macrolide citrate salt, a filler, and at least one hydrophilic polymer to form a first mixture of the multiple components, granulating the mixture in the presence of a binder to form granules which are dried, properly sized and lubricated to form an oral controlled release solid dosage formulation, wherein the granulating step is performed slowly, such that a solvent or a mixture of solvent and binder is added in small amounts to the first mixture. The method may further comprise compressing the lubricated granules to form a tablet and/or coating the oral controlled release solid dosage formulation.

The macrolide citrate salts according to preferred embodiments of formulations and methods are made by a method comprising dispersing a macrolide in an organic solvent, adding an aqueous solution comprising citric acid to the macrolide to form a mixture, and removing the organic solvent from the mixture to form a macrolide citrate salt, wherein the citric acid and macrolide are present in substantially equimolar quantities. The method may further comprise washing the macrolide citrate salt with cold water and drying the salt/evaporating the water. The methods may further comprise characterizing the isolated macrolide citrate salt by analyzing at least one property of the isolated citrate salt, such as assessing its melting point, assessing its stability, assessing its pH solubility, assessing its water content, assaying the salt by high performance liquid chromatography (HPLC) or assaying the salt by differential scanning calorimetry (DSC).

In preferred embodiments of the formulations and methods, the macrolide is clarithromycin or roxithromycin; the filler is selected from the group consisting of lactose, starches, glucose, sucrose, mannitol, and cellulose; at least one hydrophilic polymer is selected from the group consisting of povidone, hydroxypropyl cellulose, hydroxypropyl methyl cellulose, methyl cellulose, and methacrylic acid copolymers; and/or the organic solvent is acetone. In preferred embodiments, the controlled release pharmaceutical formulation is in solid oral dosage form, such as a tablet, with a strength of 500 mg of clarithromycin, preferably adapted for a single dose regimen per day.

In a further embodiment, there is provided a pharmaceutical composition for the extended release of an erythromycin derivative in the gastrointestinal environment, comprising of the citrate salt of an erythromycin derivative, more particularly of clarithromycin, and a pharmaceutically acceptable polymer, so that its Dissolution Profile is equivalent to that of commercially available products and to that of a similar composition using physical mixture of drug and citric acid in place of the salt, with F2 values ranging from 63 to 67.

DETAILED DESCRIPTION OF THE PREFERRED EMBODIMENT

Figure 1:
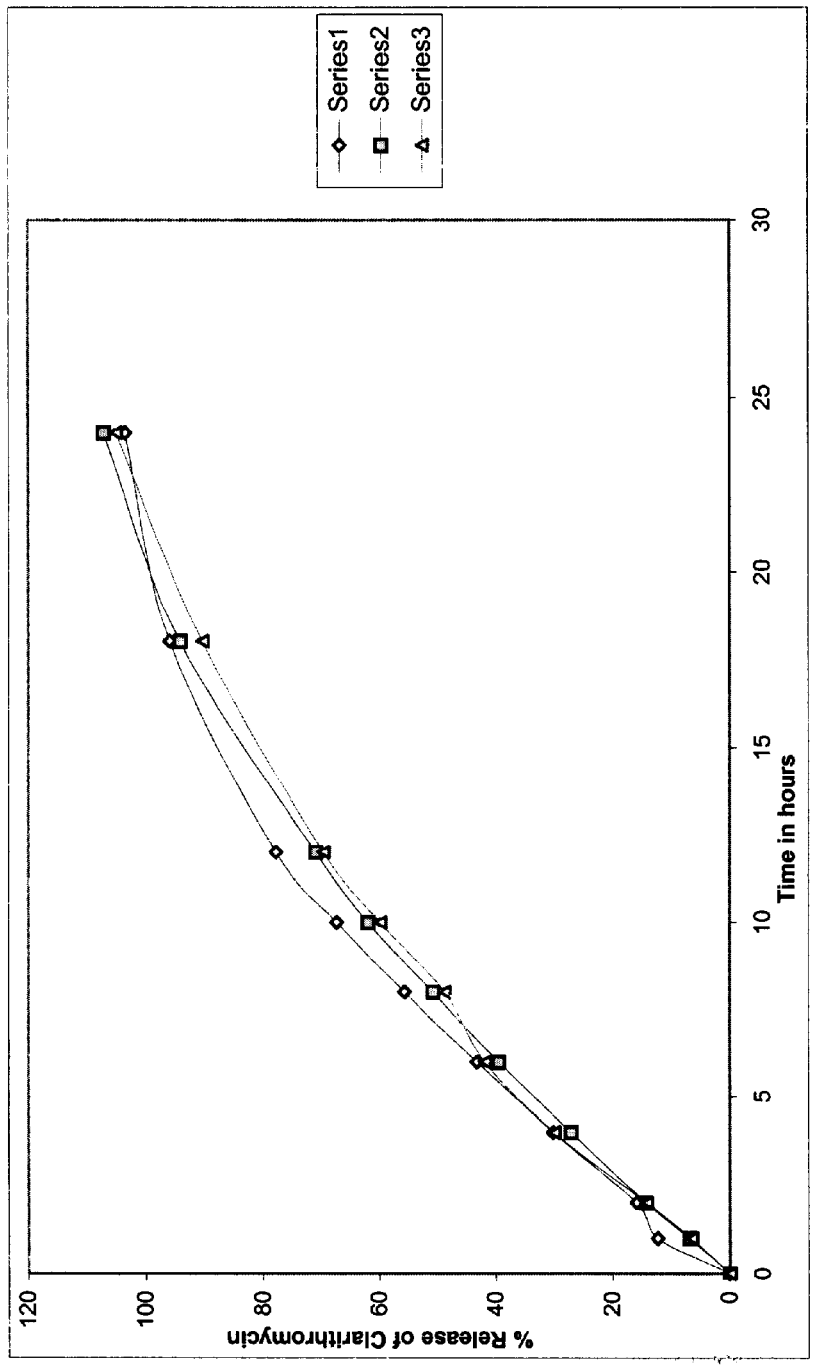
FIG. 1 shows Comparative Dissolution profiles of clarithromycin in its Controlled release tablet-500 mg made by different methods. The Dissolution medium contained 0.05M Phosphate Buffer—pH 6.8 (900 ml); the analytical method employed was HPLC Method of Clarithromycin, USP; the tablet type was oblong, yellow and film coated; and the packaging type was Blister Pack. Series 1 corresponds to a formulation comprising clarithromycin citrate salt according to a preferred embodiment of the present invention (B.No.RD-12R2); Series 2 corresponds to the reference formulation, Biaxin-XL™ (Abbott Labs); and Series 3 corresponds to a formulation comprising a physical mixture of clarithromycin and citric acid (B.No.RD-17).

The citrate salt of a macrolide, especially of clarithromycin, when isolated after preparation and characterization, overcomes the disadvantages of poor and pH-dependent solubility of the pure drug and the disadvantages of drug instability of the physical mixture of the drug with citric acid. This citrate salt, when used in an oral controlled slow release tablet of macrolide antibiotic, especially of clarithromycin, along with a pharmaceutically acceptable polymer, gives a dosage form which is bioequivalent to that of commercially available products and at the same time has the advantages of excellent stability, reproducible release pattern after aging and repeatable dissolution profiles between different batches.

Presented herein is a comparison of Stability Data and Impurity Profiles of the controlled release pharmaceutical compositions made with the citrate salt of clarithromycin and with the physical mixture of drug and citric acid using all other excipients and polymers same. The oral controlled release tablet with the citrate salt was found to be extremely stable with a very good Impurity Profile of clarithromycin as per E.P. in comparison to the other one.

Also presented herein are studies on the effect of aging on the dissolution of clarithromycin in the above mentioned two dosage forms. The disadvantage of slowing down of dissolution of drug with aging in physical mixture was not there in the case of tablet with citrate salt of clarithromycin.

Also presented herein are studies on the repeatability of dissolution profiles of different batches of oral controlled release tablet using clarithromycin citrate salt with minor variations in the excipients. All the batches checked were similar to each other with F2 values ranging from 57 to 71.

Also presented herein are studies on the bioequivalence of the single dose of oral controlled slow release tablet of clarithromycin (500 mg) comprising of its citrate salt, with a single dose of a similar commercially available product. A randomized, two treatment, two way, two period, single dose, cross over pharmacokinetic Bioequivalence Study in healthy adult male volunteers of the above mentioned two products showed all pharmacokinetic parameters i.e. $C_{max}$, $T_{max}$, AUC, $C_{min}$ etc. equivalent to each other and to published reports. The longer $T_{max}$ and lower $C_{max}$ values than that of Immediate Release (IR) product of clarithromycin suggest that the composition of the invention is an Extended Release (ER) product with a less tendency to produce gastrointestinal and other adverse effects associated with IR product, with no compromise at the same time in AUC and $C_{min}$ showing therapeutic equivalence with better patient compliance.

In an attempt to develop the oral controlled release formulation of clarithromycin using citric acid (to increase the solubility of the drug) and different polymers, some very interesting observations came up during the experiments. It was found that when clarithromycin was mixed with citric acid physically in equimolar ratio along with lactose, polymers and povidone, the screened and thoroughly blended mixture then granulated using a 50:50 v/v solution of alcohol and water, most of the time, some spots appeared on the tablet surface within 1–3 days at high temperature (in these examples, 60° and 85° C.), which increased and darkened within 7–15 days. Though the speed and intensity of this spotting depended upon the method of granulation used, it was present in almost all the experiments done, as follows:

a) Fast Granulation

When the procedure of granulation was done at a fast speed using same procedure as mentioned above, the tablets showed wet yellow spots within 2 days at 85° C. which worsened and became brownish with an uneven surface within another 2 to 3 days. Even at 40° C. and 75% RH, the tablets showed light brown spots with rough appearance just after 19 days.

b) Separate Granulation of Clarithromycin and Citric Acid

It was presumed that the above-mentioned spotting occurs because macrolides are unstable in the presence of acids. Hence clarithromycin and citric acid were not mixed together but were granulated separately using the same ingredients. Several reddish spots appeared both at 40° C. and 75% Relative Humidity (RH) and at 60° C. within 7–8 days.

c) Fast Granulation using both Alcoholic and Hydroalcoholic Solvent

Results were same as in (a).

d) Separation of Polymer from Granulation

Results were same as in (a).

e) Slow Granulation

When the physical mixture of clarithromycin, citric acid, lactose and polymers like that used in (a) was granulated slowly using small amounts of solvent, tablets were better. Very light pinkish brown spotting appeared slowly at 85° C. after 3 days and nothing happened at 60° C. and at 40° C./75% RH for 30 days.

It was felt that the best results were obtained when the granulation was done slowly, (i.e. by adding the solvent in several small aliquots over a longer period of time rather than a few larger aliquots or all at once in a relatively short period of time), after mixing clarithromycin and citric acid directly with each other, while worst results were obtained when the two were granulated separately. It means that some reaction, is taking place between clarithromycin and citric acid which if allowed to complete may result in the most stable product. This led first to the isolation of the citrate salt of clarithromycin and use the same after characterization and standardization for the preparation of its controlled release tablet in order to get reproducible results as far as solubility, stability and release pattern of clarithromycin are concerned.

It should be noted that use herein of the term "equimolar" means that substantially the same number of moles are utilized. The amounts may vary from exactly equimolar by 2–5% or more and still be equimolar.

Preparation of Clarithromycin/Roxithromycin Citrate Salt

Clarithromycin/Roxithromycin was dispersed in sufficient amount of acetone. Although acetone is preferred, other organic solvents may be used. Preferred organic solvents are miscible with water, do not react with the drug and citric acid, and/or have a relatively high vapor pressure. Citric acid was taken in equimolar ratio and dissolved separately in little water. Other aqueous solutions may also be used, provided that they do not interfere with formation of the salt. The citric acid solution was added to the slurry of drug slowly while stirring which first solubilized the drug and then resulted in the formation of the salt during further stirring and gradual evaporation of acetone. Alternatively, following salt formation, the evaporation of solvent may proceed by any suitable means, including filtration, heat, reduced pressure (vacuum), desiccants, and combinations of such methods, all of which are intended to be included in the term "evaporate". This salt was washed with little cold water and dried at 40–45° C. Other solvents may be used for the wash, such as alcohol, and blends of solvents, and other drying temperatures and methods (as noted above) may be used. The material thus prepared when tested was found to have properties absolutely different from that of pure drug as well as from that of its physical mixture with citric acid as shown in Table-I.

TABLE I

Comparative Data of Clarithromycin Citrate Salt with Clarithromycin and Physical Mixture of Clarithromycin and Citric Acid

| S. No. | Parameters | Clarithromycin | Physical Mixture of Clarithromycin and Citric Acid | Clarithromycin Citrate salt |
|---|---|---|---|---|
| 01. | Melting Point | 220–224° C. | 137° C. | 207–210° C. |
| 02. | pH of 0.2% suspension in water: methanol (19:1) | 7.5 to 10.0 | 3.5–4.5 | 3.5–4.5 |
| 03. | Assay by HPLC (on as such basis) | NLT 970 mcg/mg | 740–770 mcg/mg | 740–770 mcg/mg |
| 04. | Water Content (by Karl Fischer) | NMT 2% w/w | 2.5–4% w/w | 5–8% w/w |
| 05. | pH solubility studies (mg of Clarithromycin dissolved per ml of buffer) | | | |
| | pH 3.0 (KCl Buffer) | 2.00 mg/ml | 15.10 mg/ml | 13.65 mg/ml |
| | pH 4.0 (KCl Buffer) | 0.33 mg/ml | 15.60 mg/ml | 14.29 mg/ml |
| | pH 5.0 (Phosphate Buffer) | 10.09 mg/ml | 15.34 mg/ml | 13.77 mg/ml |
| | pH 6.0 (Phosphate Buffer) | 7.46 mg/ml | 14.65 mg/ml | 14.15 mg/ml |
| | pH 7.0 (Phosphate Buffer) | 2.00 mg/ml | 15.10 mg/ml | 14.36 mg/ml |
| 06. | Stability Studies | | | |
| | 85° C.-1 day | No Change/No Degradation | Color changes | No Change/No Degradation |
| | 85° C.-4 days | No Change/No Degradation | Very bad appearance, black colored with lump formation and foul smell. Degradation of Clarithromycin 31.41% | No Change/No Degradation |
| | 85° C.-7 days | No Change/No Degradation | Degradation-38.98% (With foul smell more prominent) | No Change/No Degradation |
| | 85°-15 days | No Change/No Degradation | Degradation-46.04% | No Change/No Degradation |
| | 60° C.-1 month | No Change/No Degradation | Degradation-11.99% (Light brown colored) | No Change/No Degradation |
| | 60° C.-2 months | No Change/No Degradation | Degradation-20.55% (Dark brown with bad smell) | No Change/No Degradation |
| | 60° C.-3 months | No Change/No Degradation | Degradation-27.73% | No Change/Degradation 3.24% |
| | 40° C. and 75% RH-2 Months | No Change/No Degradation | Degradation-20.81% (Dark Brown with bad smell) | No Change/Degradation 3.42% |
| | 40° C. and 75% RH-3 Months | No Change/No Degradation | Degradation-32.72% | No Change/Degradation 3.77% |
| | RT-3 Months | No Change/No Degradation | Degradation-2.45% | No Change/No Degradation |
| | 40° C. and 75% RH-4 Months | No Change/No Degradation | Degradation-33.93% | No Change/Degradation-4.04% |
| | 40° C. and 75% RH-5 Months | No Change/No Degradation | Degradation-37.07% | No Change/Degradation-4.21% |
| | RT-6 Months | No Change/No Degradation | Degradation-2.30% | No Change/No Degradation |
| | RT-9 Months | No Change/No Degradation | Degradation-2.17% | No Change/No Degradation |
| | RT-12 Months | No Change/No Degradation | Degradation-2.17% | No Change/No Degradation |
| 07. | Differential scanning Calorimetry (DSC) Experimental conditions: Sample pan-Alu. crucible, 40 μl, sealed with pinhole Reference Pan-same type as above, empty Temp. range-25° to 350° C. with a rise of 10° C./min under $N_2$ atmosphere at 80 ml/min | (1) Drug Peak at 227.50° C. (226.23°–229.60° C.) | (a) Fresh Mixture 1) Citric acid peak at 73.63° C. (62.52°–78.84°) 2) A broad peak (mixture of peaks) at 191.89° C. (182.10°–214.35° C.) b) 3 months old mixture kept at RT (1) Peak at 145.35° C. (138.50°–148.57° C.) (2) A broad peak (mixture of peaks) at 176.11° C. (170.05°–197.65° C.) | (1) Drug Peak at 219.05° C. (215.76°–223.30°) (2) Water peak at 89.49° C. (70.45°–96.36° C.) |

Table-I illustrates that clarithromycin, though quite stable, has the disadvantage of very poor and pH dependent solubility. This disadvantage though overcome by the physical mixture of clarithromycin and citric acid in equimolar ratio, the end product is very unstable as shown by the accelerated stability studies and DSC curves. Both these ingredients start reacting with each other the moment they are mixed together in dry form as shown by the peaks of Differential Scanning Calorimetry (DSC) of fresh and 3 months old mixture. Citric acid peak at 73.63° C. is present only in freshly prepared physical mixture and not in 3 months old mixture kept at RT with no sharp peak of drug at about 220° C. in either of them as present in DSC of pure drug or of its citrate salt. Rather a broad peak at 191.89° C. starting from 182.1° C. to 214.35° C. (showing a mixture of many peaks) is present which indicates the absence of drug clarithromycin in intact form.

Clarithromycin citrate salt has the combined advantages of both—the advantage of high stability of pure drug and the advantage of high and pH independent solubility of its physical mixture. This salt on thermo-gravimetric analysis showed external solvent and moisture content to be 2.46% (at 59.92° C.) and water of hydration equal to 2.09% at 71.97° C., which comes out to be equivalent to one molecule of water of hydration. The presence of 1:1 molar ratio of clarithromycin and citric acid along with one molecule of water of hydration in the salt was further confirmed by the elemental analysis where % carbon was found to be 52.89%, % nitrogen—1.24% and % hydrogen—8.28%.

Similar pattern was observed in the case of roxithromycin citrate. It showed a much higher and pH independent solubility as compared to pure roxithromycin till pH 6.00 and much better stability as compared to its physical mixture, the latter turning moist, dark-colored with foul smell just after 4 days at 85° C., in the same way as in the case of clarithromycin. The content of drug was 760–790 µg/mg (on as such basis) and water equal to 6–8% in the salt. DSC curves showed single peaks for both—roxithromycin (melting point 127° C.) and its citrate salt (melting point 122° C.) at 122.51° C. and 120.03° C. respectively. The physical mixture of roxithromycin and citric acid (freshly prepared) showed two peaks in DSC at 73.36° C. (of citric acid) and at 122.74° C. (of roxithromycin). TGA curve showed external moisture and solvent to be equal to 3.35% (at 60.94° C.) and water of hydration equal to 3.10% at 91.54° C., the latter being equivalent to two molecules of water of hydration.

All the above data clearly shows that by salt formation by reacting macrolide antibiotics e.g. clarithromycin and roxithromycin with organic carboxylic acid e.g. citric acid, their three main disadvantages i.e. poor solubility, pH-dependent solubility and instability in the presence of free acids can be overcome. Moreover, if the physical mixture is used in any oral solid dosage form (tablet, capsule or dry syrup), there may always be a risk of non-reproducibility of release pattern of drug due to incomplete reaction between the drug and acid under different manufacturing conditions as shown in different experiments mentioned above.

However if the completely reacted material i.e. the citrate salt is used, consistent release pattern is obtained irrespective of manufacturing conditions (granulation) and shelf life. Also the risk of having any detrimental effects of free acid on the drug during its shelf-life is eliminated by using the citrate salt of macrolide antibiotics in pharmaceutical dosage forms.

Manufacture of Controlled Release Tablet of Macrolide Antibiotics using their Isolated Citrate Salt Clarithromycin citrate salt as prepared above showed very high and pH independent solubility along with excellent stability. Hence it was decided to use it for preparing a Controlled Release tablet for single daily dose to provide 500 mg of clarithromycin in a 24 hours period. The pharmaceutical composition according to preferred embodiments comprises a pharmaceutically active compound and a pharmaceutically acceptable polymer. The pharmaceutically active compound is the citrate salt of an erythromycin derivative. Preferably, the erythromycin derivative is 6-O-methyl erythromycin A, known as clarithromycin. The amount of the citrate salt (equivalent to 500 mg of clarithromycin) varies from about 65% to about 80% by weight of the composition. Preferably, the composition comprises about 70% by weight of the citrate salt of clarithromycin.

The pharmaceutically acceptable polymer is a water-soluble hydrophilic polymer selected from the group consisting of Povidone, Hydroxypropyl Cellulose, Hydroxypropyl Methyl Cellulose, Methyl Cellulose, Methacrylic acid copolymers etc. Preferably, the polymer is selected from Hydroxypropyl Cellulose, Hydroxypropylmethyl Cellulose and Methyl Cellulose. More preferably, the polymer is Hydroxypropylmethyl Cellulose of two different grades. Most preferably, one polymer is a high viscosity Hydroxypropylmethyl Cellulose with percent Methoxy group ranging from 19.0–24.0, percent Hydroxypropoxy group ranging from 4.0–12.0, and viscosity in cp ranging from 11,250–21,000. The most preferred polymer in this group (USP Substitution Type 2208) is a high viscosity Hydroxypropylmethyl Cellulose with a viscosity of about 15,000 cp, commercially available under the Trade name Methocel K-15 M™ from Dow Chemical Company.

Another polymer is also a high viscosity Hydroxypropylmethyl Cellulose but with lower viscosity than the above mentioned i.e. ranging from 3000 to 5600 cp. Also the percent Methoxy group is different, ranging from 28.0–30.0 and percent Hydroxypropoxy group ranges from 7–12. The most preferred polymer in this group (USP Substitution Type 2910) is a high viscosity Hydroxypropyl Methyl Cellulose with a viscosity of about 4000 cp., commercially available under the Tradename Methocel E4M™ from Dow Chemical Company.

The amount of the polymers in the composition generally varies from about 5% to about 15% by weight of the composition. Preferably, the amount of polymers varies from about 5% to about 10% by weight of the composition. More preferably, the amount of polymer varies from about 6% to about 8% by weight of the composition. The composition usually comprises pharmaceutically acceptable excipients and/or fillers and extenders (these terms are used interchangeably herein) such as lactose, starches, glucose, sucrose, mannitol, microcrystalline cellulose, other celluloses; and may further comprise lubricants such as talc, calcium stearate, magnesium stearate, solid polyethylene glycols etc. The amount of lubricants generally varies from about 0.5% to about 10% by weight of the composition. Preferably, the lubricants used are Magnesium Stearate and Talc in the total amounts ranging from about 1.0% to about 5% by weight of the composition. The amount of fillers and extenders varies from about 10% to about 40% by weight of the composition/formulation. A particular preferred composition for the extended release of the active compound therefrom comprises:

About 665 mg of clarithromycin citrate salt equivalent to about 500 mg of clarithromycin; and from 36 to 100 mg of Methocel K 15 M™; and from 24 to 40 mg of Methocel E 4M™

The formulations are generally prepared by dry blending the active drug i.e. citrate salt of erythromycin derivative with polymers, fillers and other excipients (all passed through a minimum of 250 μm aperture screen) followed by wet granulation using binders soluble in hydroalcoholic solvents e.g. Povidone. The granulation is done by methods known in the art. The wet granules are dried, sifted and ground to appropriate size. Lubricating agents (also passed through a minimum of 250 μm aperture screen) are mixed with the dried granulation to obtain the final formulation.

The compositions of the invention can be administered orally in the form of tablets, capsules, pills, granules or dry syrups. The tablets can be prepared by compressing the above mentioned lubricated granules using suitable punches and dies. Tablets and pills/granules can additionally be protected with film coatings, enteric coatings and other release-controlling coatings for the purpose of light protection and taste-masking. The coating may be colored with a pharmaceutically acceptable dye. The amount of dye and other excipients in the coating liquid may vary without having any effect on the performance of extended release dosage forms.

The coating liquid generally comprises of film forming polymers such as hydroxypropyl Cellulose, hydroxypropylmethyl Cellulose, Cellulose Ester or Ether, an acrylic polymer or a mixture of polymers. The coating solution can be an aqueous or hydroalcoholic solution further comprising of plasticizers such as glycols, Castor oil, Triethyl citrate, opacifying agents such as titanium dioxide, anti-adherents such as talc, magnesium stearate, glyceryl monostearate and a pharmaceutically acceptable dye.

The daily dose of the composition of this invention administered to the patient in a single dose can be in the amounts from 500 mg to 1000 mg once-a-day for five to fourteen days.

Stability Data, Dissolution and Impurity Profiles of Clarithromycin Controlled Release Tablets The film coated controlled release tablets made with clarithromycin citrate salt (RD/12 $R_2$) when studied for their Dissolution Profile in pH 6.8 phosphate buffer, showed very similar release pattern as compared to the coated one made with equivalent quantities of clarithromycin and citric acid in the form of physical mixture (RD/17) as well as to that of the commercially available product (FIG. 1), with similarity factor—F2 value equal to 63 to 67.

Figure 2:
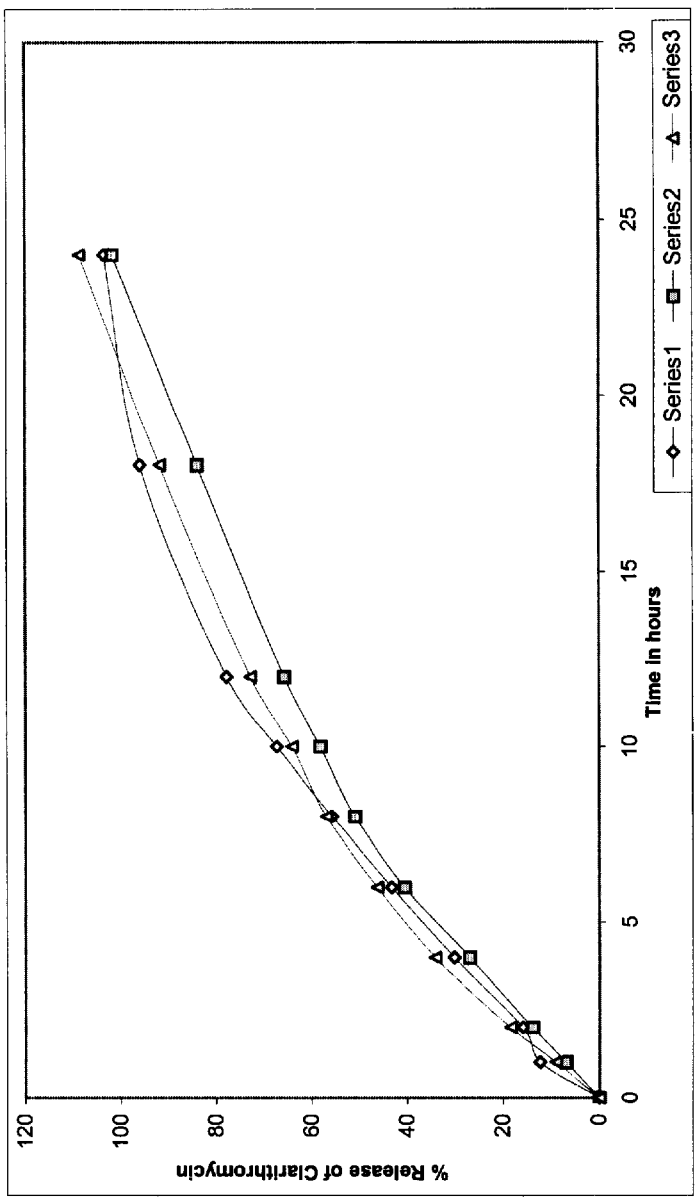
FIG. 2 shows Comparative Dissolution profiles of clarithromycin in its Controlled release tablet-500 mg in different batches made by using clarithromycin citrate salt according to preferred embodiments of the present invention. The Dissolution medium contained 0.05M Phosphate Buffer—pH 6.8(900 ml); the analytical method employed was HPLC Method of Clarithromycin, USP; the tablet type was oblong, yellow and film coated; and the packaging type was Blister Pack. Series 1 corresponds to batch RD-12R$_2$; Series 2 corresponds to batch RD-22C; and Series 3 corresponds to batch RD-27 I.

Different batches prepared using clarithromycin citrate salt and using similar manufacturing formula and procedure as RD/12 $R_2$ (with minor variations) showed very good repeatable dissolution profiles (FIG. 2), with F2 values equal to 57 to 71, a feature lacking in the Alignate matrix tablet (Ref. Patent No. WO/00/48607).

In order to compare the exact differences in the stability and release pattern of clarithromycin after aging in the CR tablets made by clarithromycin citrate salt and made by physical mixture of clarithromycin and citric acid, two batches RD/16 and RD/17 were prepared at the same time using exactly the same excipients, polymers etc. and in the same quantities except that in RD/16, clarithromycin citrate salt equivalent to 500 mg of clarithromycin was used while in RD/17, equivalent quantities of drug and citric acid were used in the form of physical mixture. The tablets were compressed, film coated, blister packed and stored under the same conditions (as per ICH guidelines), for 4 months at accelerated conditions 40° C./75% RH and for 2 months at stress conditions, 60° C. Samples of both were analyzed monthly for the content of clarithromycin and all possible impurities of clarithromycin mentioned in European Pharmacopoeia (Ref. Pharmeuropa, Vol. 13, No. 4, October '2001, p. 752).

It was observed that in the case of RD/17, there was an appreciable increase in Impurities especially Impurity I (3-O-decladinosyl-6-o-methylerythromycin A) just after 2 months at 60° C., Imp. I going up to 0.62% and after 3 months at 40° C./75% RH, going up to 0.29% which failed as per E.P. (E.P. limit for Imp. I is 0.2%). Some unknown impurities also appeared at 60° C. in RD/17, much higher than the EP limit Degradation of clarithromycin went up to 2% at 60° C. (2 months) and 2.94% at 40° C./75% RH (3 months) in RD/17 as compared to 0.92% at 60° C. (2 months) and 2.15% at 40° C./75% RH (3 months) in RD/16 with all the impurities including Impurity I, well within EP limits (Imp.I at 60° C., 2 months—0.19%; at 40° C./75% RH, 3 months—0.18%). The increase in Imp.I only in the case of physical mixture tablet i.e. RD/17 was due to the presence of free citric acid in it as Imp. I has been reported to increase in the presence of acid at high temperature.

Figure 3:
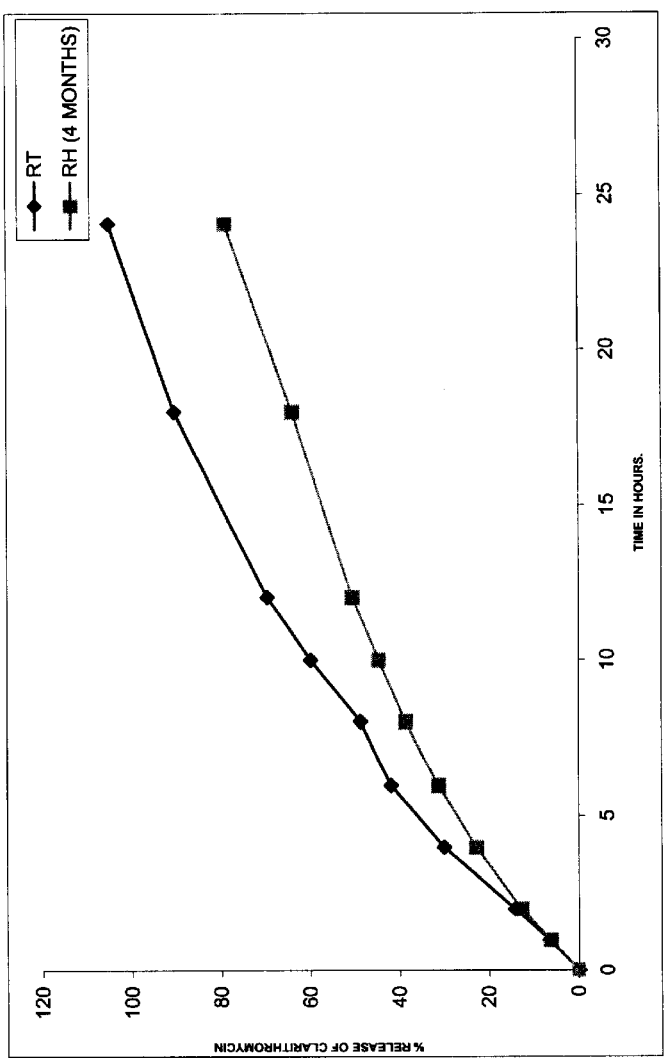
FIG. 3 shows Comparative Dissolution Profile of clarithromycin in its Controlled release tablet (500 mg) using the Physical Mixture of equimolar quantities of clarithromycin and citric acid, stored at Room Temperature (RT) and at 40° C./75% relative humidity (RH) for 4 months. The Dissolution medium contained 0.05M Phosphate Buffer—pH 6.8 (900 ml); the analytical method employed was HPLC Method of Clarithromycin, USP; the tablet type was oblong, yellow and film coated; and the packaging type was Blister Pack. The batch number depicted was RD-17.
Figure 4:
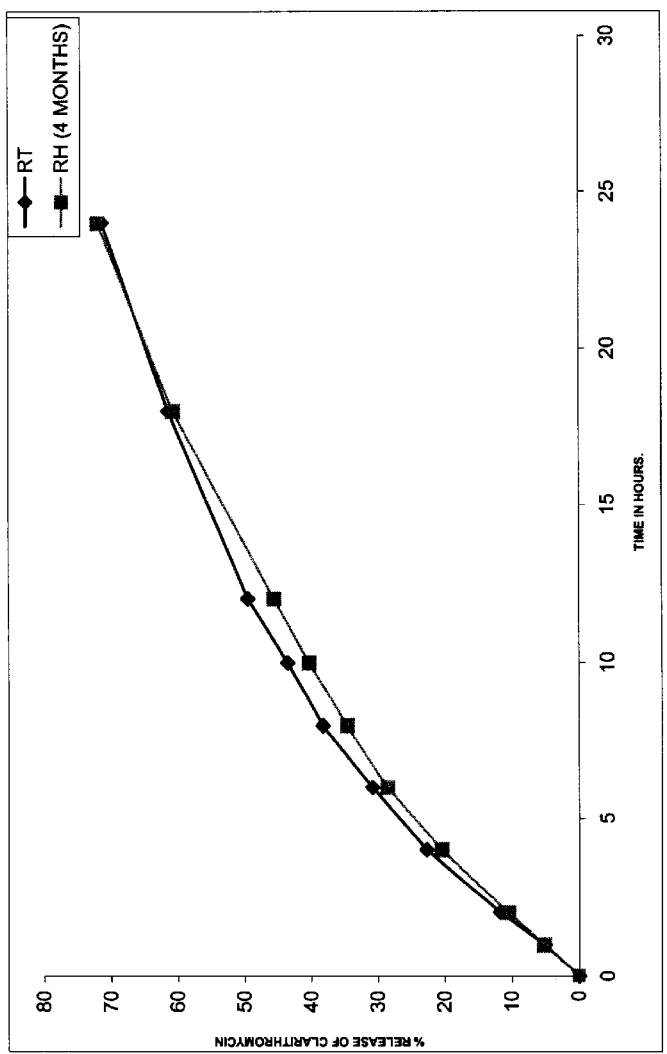
FIG. 4 shows Comparative Dissolution Profile of Clarithromycin in its Controlled release tablet (500 mg) using clarithromycin citrate salt, stored at Room Temperature (RT) and at 40° C./75% RH for 4 months. The Dissolution medium contained 0.05M Phosphate Buffer—pH 6.8 (900 ml); the analytical method employed was HPLC Method of Clarithromycin, USP; the tablet type was oblong, yellow and film coated; and the packaging type was Blister Pack. The batch number depicted was RD-16.

Other than the Impurity Profiles, the Dissolution Profiles of both the above batches were also studied after storage at 40° C./75% RH for 4 months in blister packed condition and compared with the initial. FIG. 3 shows the comparative Dissolution Profiles of RD/17 at RT and RH (4 months) while FIG. 4 shows the same comparison for RD/16. It can be clearly seen that there is a drastic reduction in the rate of release of clarithromycin after 4 months at RH in case of RD/17 but it remains almost same in RD/16. Thus the disadvantage of slowing down of dissolution of clarithromycin with aging, which has been disclosed in patent No. WO/00/48607 for Extended Release tablets of clarithromycin containing physical mixture of drug and Citric acid in an alginate matrix, has also been overcome by using citrate salt of macrolides.

Thus the assumptions, on the basis of which the citrate salt of macrolides was used in the matrix of its controlled release tablet, were found to be true as shown by the Stability Data and Dissolution Profiles mentioned above. The main advantages i.e. excellent stability, reproducibility of release pattern after aging, least variation between dissolution profiles of different batches and efficient release of clarithromycin in a controlled manner throughout a 24 hours period can be easily seen.

Bioequivalence Study

The bioequivalence study of a single dose of Oral Controlled slow release tablet of clarithromycin citrate salt equivalent to 500 mg of clarithromycin was carried out in comparison to a single dose of Biaxin-XL™ (500 mg) of Abbott Labs., U.S.A., using a randomized, two treatment, two way, two period, single dose, cross over pharmacokinetic study in healthy adult male human subjects under fasting conditions.

Plasma samples collected at different time intervals up to 48 hrs. were assayed for clarithromycin using a validated High-performance Liquid Chromatographic Procedure using Electrochemical Detector described in Reference— "Comparison of bronchopulmonary pharmacokinetics of clarithromycin and Azithromycin," *Antimicrob. Agents Chemother* (1996) v40, pages 2375–2379.

EXAMPLE 1

Preparation of CR Formulation of Clarithromycin (500 mg) using its Isolated Citrate Salt

| Ingredients | Quantity (mg/tablet) |
|---|---|
| Clarithromycin Citrate Salt (having a potency of 765 µg of Clarithromycin per mg of salt on as such basis) equivalent to 500 mg of Clarithromycin U.S.P. | 653 |
| Lactose (monohydrate) U.S.P. | 100 |
| Starch-1500 ™ (Pregelatinised Starch) | 30 |
| Povidone K-30 U.S.P. | 36 |
| Ethyl Alcohol:Purified Water (90:10) | qs |
| Methocel K 15 M ™ (Premium EP) | 36 |
| Methocel E 4M ™ (Premium CR EP) | 24 |
| Magnesium Stearate U.S.P. | 9 |
| Talc U.S.P. | 9 |
| Sodium Starch Glycollate U.S.P. | 15 |
| Starch-1500 ™ | 15 |

Method of Preparation of CR Tablet of Clarithromycin (500 mg) using its Citrate Salt The citrate salt of clarithromycin after passing through 60# mesh was dry mixed with lactose (100# mesh) and starch-1500 (60# mesh—30 mg/tablet) in a Rapid Mixer Granulator (RMG). The thoroughly blended mixture was then granulated using a hydroalcoholic solution (90:10) of Povidone K-30 in RMG till proper granules of 18# mesh were formed. These dried granules were then geometrically mixed with Methocel K-15M™ (60# mesh) and Methocel E-4M™ (100# mesh) (both of Dow Chemical Co.) along with other lubricants (60# mesh). The mixture was slugged, and then sieved through 22 # mesh to be recompressed again using oblong Punches and Dies (length 20.10±0.1 mm; width 9.63±0.05 mm) at an average weight of about 927 mg and thickness of 6.40±0.1 mm. The tablets having negligible friability and good hardness were film coated for elegance and taste masking using Opadry™ white of Colorcon, Asia and Quinoline Yellow as the coloring agent (coating equal to 2–3% of weight gain). They were blister packed after complete drying and testing.

EXAMPLE 2

Preparation of Controlled Release Formulation of Clarithromycin using its Isolated Citrate Salt The citrate salt of clarithromycin equivalent to 500 mg of clarithromycin was dry-mixed with Methocel K-15 M™, Methocel E 4M™ of Dow Chemical Co., and lactose (monohydrate), (after passing each of them through a minimum 250 µm aperture screen) in a Rapid mixer granulator (RMG). The thoroughly blended mixture was granulated in the same RMG using a hydroalcoholic solution of Povidone until a proper granulation was obtained. The granules were then dried, sifted and ground to appropriate size. Talc, magnesium stearate and starch derivatives were passed through a 250 µm aperture screen and mixed with the dried granules. The lubricated granules were then loaded in the hopper of compression machine and compressed to form oblong tablets of about 920 mg weight of suitable thickness, hardness and friability. The tablets were then film coated (about 2% of the tablet weight) for elegance and taste masking using Opadry™ White of Colorcon, Asia and Quinoline Yellow as the coloring agent. Three examples of different formulations A, B and C are shown below in Table-2, prepared according to the general method described above.

TABLE 2

| Ingredient | A (mg/tablet) | B (mg/tablet) | C (mg/tablet) |
|---|---|---|---|
| Clarithromycin Citrate Salt (740–770 mcg/mg on as such basis) equivalent to 500 mg of Clarithromycin U.S.P. | 675 | 675 | 675 |
| Methocel K 15 M ™ (Premium EP) | 36 | 48 | 60 |
| Methocel E 4 M ™ (Premium CR EP) | 24 | 32 | — |
| Lactose, Monohydrate USP | 100 | 100 | 100 |
| Povidone (PVP) K-30 USP | 25 | 40 | 40 |
| Magnesium Stearate USP | 10 | 10 | 10 |
| Talc USP | 10 | 10 | 10 |
| Sodium Starch Glycolate USP | 30 | 20 | 30 |
| Purified Water USP | qs | qs | qs |
| Ethyl Alcohol | qs | qs | qs |

EXAMPLE 3

Figure 5:
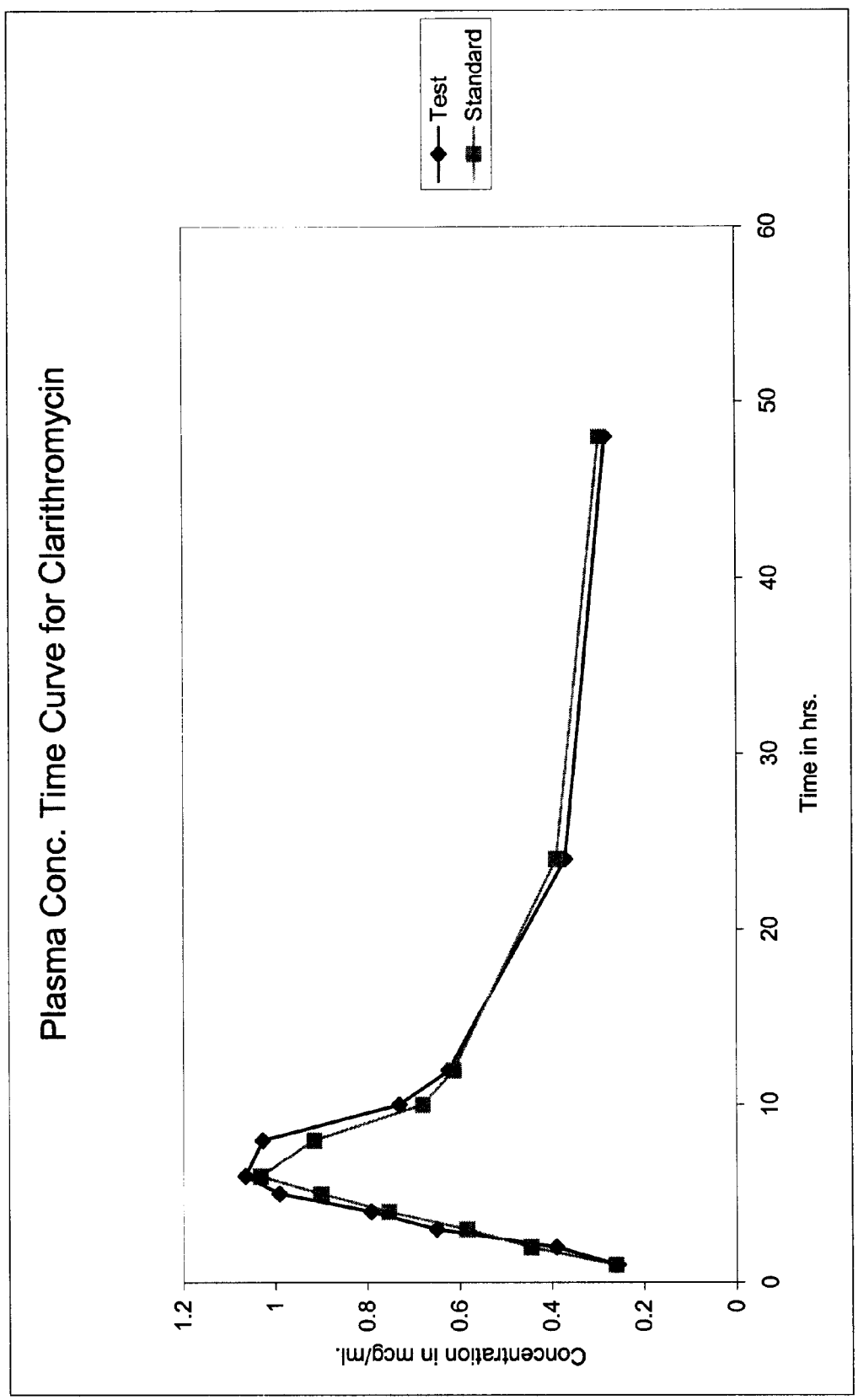
FIG. 5 shows Comparative Plasma concentration—Time curve for Clarithromycin 500 mg CR tablets (Test comprising equivalent quantity of clarithromycin citrate salt, B.No.RD 27I) versus a reference formulation (Biaxin-XL™).

The bioequivalence study of a single dose of Oral Controlled slow release tablet of clarithromycin citrate salt equivalent to 500 mg of clarithromycin was carried out in comparison to a single dose of Biaxin-XL™ (500 mg) of Abbott Labs., U.S.A., using a randomized, two treatment, two way, two period, single dose, cross over pharmacokinetic study in healthy adult male human subjects under fasting conditions. The human volunteers were selected from the age group of 18–35 years. They were medically fit persons with normal weight to height ratio, with no history of allergy to drug or any infections disease or any liver, kidney or cardiovascular disorder or alcoholism or drug dependence. They were screened after a complete physical, biochemical and hematological examination. Each subject received a single dose of 500 mg clarithromycin (ER) tablets (either standard or test sample depending on the randomization chart) after overnight fasting. No food was allowed for 2 hours after swallowing the tablet. Standard diet was provided to the volunteers during the study. After a washout period of 7 days, every volunteer was crossed on to the other formulation. Blood samples were collected prior to dosing (0 hr.) and at 1.0, 2.0, 3.0, 4.0, 5.0, 6.0, 8.0, 10.0, 12.0, 24.0 and 48.0 hrs. after dosing. The collected blood samples were transferred to heparinized collection tubes and centrifuged, to be stored at −20° C. until the time of analysis. Plasma samples were analyzed using HPLC and ECD, the results of which showed the Plasma concentration—Time Curve for clarithromycin as shown in FIG. 5. The Comparative pharmacokinetic parameters for both, Standard and Test, are shown in Table-3.

TABLE 3

Pharmacokinetic Data

| Parameter | Reference | Test |
|---|---|---|
| $AUC_{0-24}$ mcg.h/ml | 14.304 | 14.776 |
| $AUC_{0-\infty}$ mcg.h/ml | 24.258 | 22.690 |
| $C_{max}$ mcg/ml | 1.033 | 1.066 |
| $T_{max}$ (hours) | 6.0 | 6.0 |
| $C_{min}$ (at 24 hrs.) mcg/ml | 0.389 | 0.37 |

The above data in Table-3 clearly show that the Extended Release (ER) Tablets of both Reference (Biaxin-XL™) and Test, when given at a single dose of 500 mg of clarithromycin, have all Pharmacokinetic parameters equivalent to each other with AUC's equivalent to that of a Immediate Release (IR) Product of clarithromycin (Biaxin™) given at a single dose of 500 mg as disclosed in WO 01/26663 A1 and also to that of a similar Extended Release product given at a single dose of 500 mg. (Ref. Patent Publ. No. WO 01/26663 A1). Also the $T_{max}$ i.e. 6 hrs. is almost same as mentioned in the above patent (5–5.5 hours) as compared to 2.2 brs. of IR product showing that it is an extended release product. The main advantage clear from the data given in Table 3 is that $C_{max}$ is lower than that of IR product (about 1.0 µg/ml as compared to 2.57 µg/ml of IR Product), which means that gastrointestinal and other adverse effects normally associated with clarithromycin JR tablets will be less in this ER Product of the invention leading to better patient compliance, without compromising at the same time with AUC and $C_{min}$ at 24 hrs. (latter being higher or equivalent to Minimum Inhibitory Concentration (MIC) of clarithromycin reported in literature for different micro-organisms.)

Abbreviations Used in the Text

| | |
|---|---|
| IR | Immediate Release |
| ER | Extended Release |
| CR | Controlled Release |
| $C_{max}$ | Maximum plasma concentration of the drug |
| $C_{min}$ | Minimum plasma concentration of the drug |
| AUC | Area under plasma concentration time curve calculated by trapezoidal rule over the complete time period mentioned. |
| $T_{max}$ | Time at which maximum plasma concentration of drug is achieved. |
| MIC | Minimum Inhibitory Concentration |
| GI | Gastrointestinal |

All patents and publications mentioned in the specification are indicative of the levels of those skilled in the art to which the invention pertains. All patents and publications are herein incorporated by reference in their entireties to the same extent as if each individual publication was specifically and individually indicated to be incorporated by reference.

It will be readily apparent to one skilled in the art that varying substitutions and modifications may be made to the invention disclosed herein without departing from the scope and spirit of the invention. Thus, it should be understood that although the present invention has been specifically disclosed by preferred embodiments and optional features, modification and variation of the concepts herein disclosed may be resorted to by those skilled in the art, and that such modifications and variations are considered to be falling within the scope of the invention, which is limited only by the following claims.

What is claimed is:

1. A controlled release pharmaceutical formulation comprising,
   a macrolide citrate salt;
   at least one hydrophilic polymer;
   a binder,
   a filler; and
   a lubricant;
   wherein said macrolide citrate salt is obtained by:
      dispersing a macrolide in an organic solvent;
      adding an aqueous solution comprising an equimolar amount of citric acid to said macrolide; and
      evaporating the organic solvent.

2. A controlled release pharmaceutical formulation according to claim 1, wherein the macrolide is clarithromycin or roxithromycin.

3. A controlled release pharmaceutical formulation according to claim 1, wherein the filler is selected from the group consisting of lactose, starches, glucose, sucrose, mannitol, and celluloses.

4. A controlled release pharmaceutical formulation according to claim 1, wherein said at least one hydrophilic polymer is selected from the group consisting of povidone, hydroxypropyl cellulose, hydroxypropyl methyl cellulose, methyl cellulose, and methacrylic acid copolymers.

5. A controlled release pharmaceutical formulation according to claim 4, wherein said at least one hydrophilic polymer comprises at least one polymer selected from the group consisting of hydroxypropyl cellulose, hydroxypropyl methyl cellulose, and methyl cellulose.

6. A controlled release pharmaceutical formulation according to claim 5, wherein said at least one hydrophilic polymer comprises one or more different grades of hydroxypropyl methyl cellulose and wherein said one or more grades of hydroxypropyl methyl cellulose have a viscosity from 11,250 to 21,000 centipoise and a viscosity from 3000 to 5600 centipoise.

7. A controlled release pharmaceutical formulation according to claim 1, wherein said lubricant is selected from a group comprising talc, calcium stearate, magnesium stearate and solid polyethylene glycol.

8. A controlled release pharmaceutical formulation according to claim 1, wherein said hydrophilic polymers are high viscosity Hydroxypropylmethyl Cellulose of one or more different grades, said binder is polyvinyl pyrrolidone, said fillers are lactose and starch derivatives, said lubricants are talc and magnesium stearate and said macrolide is clarithromycin.

9. A controlled release pharmaceutical formulation according to claim 1, comprising 65–80% by weight macrolide citrate salt, 5–15% by weight hydrophilic polymer, 10–40% by weight fillers and 0.5–10% by weight lubricants.

10. The controlled release pharmaceutical formulation of claim 1, wherein the formulation is a solid oral dosage form.

11. The controlled release pharmaceutical formulation of claim 10, wherein the solid oral dosage forms include tablets, capsules, pills, granules or dry syrups.

12. The controlled release pharmaceutical formulation of claim 10, wherein said formulation is adapted for a single dose regimen per day.

13. The controlled release pharmaceutical formulation of claim 10, wherein said formulation comprises a potency equivalent to 500 mg of Clarithromycin U.S.P.

14. The controlled release pharmaceutical formulation of claim 10 wherein the solid oral dosage form is a tablet.

15. A method for producing a controlled release pharmaceutical formulation of macrolide citrate salt comprising:
   mixing multiple components comprising a macrolide citrate salt, a filler, and at least one hydrophilic polymer to form a first mixture of said multiple components;
   granulating the mixture in the presence of a binder to form granules which are dried and properly sized; and
   lubricating the granules to form an oral controlled release solid dosage formulation;
   wherein said granulating step is performed slowly, such that a solvent or a mixture of solvent and binder is added in small amounts to the first mixture.

16. The method of claim 15 further comprising compressing the lubricated granules to form a tablet.

17. The method of claim 15 further comprising coating the oral controlled release solid dosage formulation.

18. The method of claim 15 wherein the macrolide citrate salt is clarithromycin citrate salt.

19. The method of claim 15 wherein the macrolide citrate salt is roxithromycin citrate salt.

20. The method of claim 15 wherein said macrolide citrate salt is made by a method comprising:
dispersing a macrolide in an organic solvent;
adding an aqueous solution comprising an equimolar amount of citric acid to said macrolide organic solution with stirring to form a second mixture; and
evaporating the organic solvent from the second mixture to form a macrolide citrate salt.

21. The method of claim 20, further comprising washing the macrolide citrate salt with a solvent selected from a group comprising water, alcohol or other blends of polar solvents.

22. The method of claim 20, further comprising washing the macrolide citrate salt with cold water and drying the salt.

23. The method of claim 20, wherein the organic solvent is acetone.

24. The method of claim 20, wherein the second mixture is further stirred after adding citric acid solution thereby causing evaporation of the organic solvent.

25. The method of claim 20, wherein the macrolide is clarithromycin or roxithromycin.

26. The method of claim 20, wherein the macrolide is clarithromycin.

27. The method of claim 20, further comprising characterizing said isolated macrolide citrate salt by analyzing at least one property of the isolated citrate salt.

28. The method of claim 27, wherein the analyzing at least one property of the isolated macrolide citrate salt comprises at least one analysis selected from the group consisting of: assessing its melting point, assessing its stability, assessing its pH solubility, assessing its water content, assaying the salt by high performance liquid chromatography (HPLC) and assaying the salt by differential scanning calorimetry (DSC).

29. A method of preparing a macrolide citrate salt, comprising:
dispersing a macrolide in an organic solvent;
adding an aqueous solution comprising citric acid to said macrolide organic solution with stirring to form a mixture; and
removing the organic solvent from the mixture to form a macrolide ciliate salt;
wherein the citric acid and macrolide are present in substantially equimolar quantities.

30. The method of claim 29, further comprising washing the macrolide citrate salt with cold water and drying the salt.

31. The method of claim 29, wherein the organic solvent is acetone.

32. The method of claim 29, wherein the mixture is further stirred after adding the aqueous solution of citric acid, thereby causing evaporation of the organic solvent.

33. The method of claim 29, wherein the macrolide is clarithromycin.

34. The method of claim 29, wherein the macrolide is roxithromycin.

35. The method of claim 29, further comprising characterizing said isolated macrolide citrate salt by analyzing at least one property of the isolated ciliate salt.

36. The method of claim 35, wherein the analyzing at least one property of the isolated macrolide citrate salt comprises at least one analysis selected from the group consisting of: assessing its melting point, assessing its stability, assessing its pH solubility, assessing its water content, assaying the salt by high performance liquid chromatography (HPLC) and assaying the salt by differential scanning calorimetry (DSC).

37. A controlled release pharmaceutical formulation according to claim 8, wherein at least one of said high viscosity Hydroxypropylmethyl Cellulose has percent Methoxy group ranging from 19.0 to 24.0, percent Hydroxypropoxy group ranging from 4.0 to 12.0, and viscosity in cp ranging from 11,250 to 21,000 cp.

38. A controlled release pharmaceutical formulation according to claim 37, wherein at least one of said high viscosity Hydroxypropylmethyl Cellulose has a viscosity of about 15,000 cp.

39. A controlled release pharmaceutical formulation according to claim 8, wherein at least one of said high viscosity Hydroxypropylmethyl Cellulose has percent Methoxy group ranging from 28.0 to 30.0, percent Hydroxypropoxy group ranging from 7 to 12, and viscosity in cp ranging from 3000 to 5600 cp.

40. A controlled release pharmaceutical formulation according to claim 39, wherein at least one of said high viscosity Hydroxypropylmethyl Cellulose has a viscosity of about 4000 cp.

41. A controlled release pharmaceutical formulation according to claim 8, wherein at least one of said high viscosity Hydroxypropylmethyl Cellulose comprises USP Substitution Type 2208 with a viscosity of about 15,000 cp, and at least one of said high viscosity Hydroxypropylmethyl Cellulose comprises USP Substitution Type 2910 with a viscosity of about 4,000 cp.

* * * * *